(12) United States Patent
Bromidge et al.

(10) Patent No.: US 6,548,504 B1
(45) Date of Patent: *Apr. 15, 2003

(54) COMPOUNDS

(75) Inventors: Steven Mark Bromidge, Sawbridgeworth (GB); Stephen Frederick Moss, Cambs (GB)

(73) Assignee: SmithKline Beecham p.l.c., Brentford (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/600,558

(22) PCT Filed: Jan. 13, 1999

(86) PCT No.: PCT/EP99/00262

§ 371 (c)(1), (2), (4) Date: Jul. 19, 2000

(87) PCT Pub. No.: WO99/37623

PCT Pub. Date: Jul. 29, 1999

(30) Foreign Application Priority Data

Jan. 22, 1998 (GB) .............................................. 9801392

(51) Int. Cl.$^7$ .................... A61K 31/495; A61K 31/505; C07D 239/02; C07D 401/00; C07D 291/00

(52) U.S. Cl. ......................... 514/252.12; 514/253.01; 514/255.03; 514/256; 514/277; 514/325; 514/372; 544/298; 544/358; 544/383; 544/392; 544/402; 544/406; 546/207; 546/225; 546/229; 546/235; 548/122; 548/125; 548/146; 548/262.2; 548/300.1; 548/400

(58) Field of Search ............................... 544/298, 359, 544/358, 383, 392, 398, 402, 406; 514/252.12, 252.18, 255.01, 253.01, 255.03, 256, 325, 372, 252.14, 277; 546/207, 225, 229, 235; 548/122, 125, 146, 206, 262.2, 300.1, 400

(56) References Cited

U.S. PATENT DOCUMENTS 3,635,982 A    1/1972  Potoski et al. ............... 260/268
6,316,450 B1 * 11/2001 Bromidge et al. ..... 514/253.05

FOREIGN PATENT DOCUMENTS

BE    620236    1/1963
DE    3411993   10/1985

(List continued on next page.)

OTHER PUBLICATIONS

Toja et al,"New classes of antimuscarinic agents . . . antispasmodic properties:";Arzneim.–Forsch. 44/4, 501–9(1994).*

(List continued on next page.)

Primary Examiner—Mukund J. Shah
Assistant Examiner—Sudhaker B. Patel

(74) Attorney, Agent, or Firm—Soma G. Simon; Mary E. McCarthy; Charles M. Kinzig

(57) ABSTRACT

The present invention therefore provides, in a first aspect, a compound of formula (I) or a salt thereof:

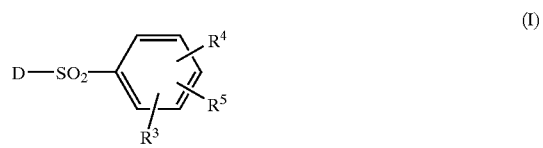

(I)

in which the group D is selected from a group of formula (A), (B) or (C) below:

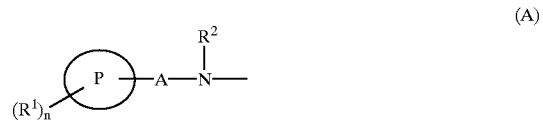

(A)

in which

P is a monocyclic, bicyclic or tricyclic alicyclic ring containing up to 20 carbon atoms in the ring(s);

A is a single bond, a $C_{1-6}$alkylene or a $C_{2-6}$alkenylene group;

$R^1$ is halogen, $C_{1-6}$alkyl optionally substituted by one or more fluorine atoms, $C_{3-6}$cycloalkyl, $C_{1-6}$alkoxy, $OCF_3$, hydroxy, hydroxy$C_{1-6}$alkyl, hydroxy$C_{1-6}$alkoxy, $C_{1-6}$alkoxy$C_{1-6}$alkoxy, $C_{1-6}$alkanoyl, amino, alkylamino or dialkylamino, $SR^{11}$ where $R^{11}$ is hydrogen or $C_{1-6}$alkyl or $R^1$ is aryl, aryl$C_{1-6}$alkyl, a bicyclic heterocyclic ring or is a 5 to 7-membered heterocyclic ring each containing 1 to 4 heteroatoms selected from oxygen, nitrogen or sulfur;

n is 0, 1, 2 or 3; and $R^2$ is hydrogen, $C_{1-6}$alkyl, aryl, aryl$C_{1-6}$alkyl or $C_{3-6}$cycloalkyl; or

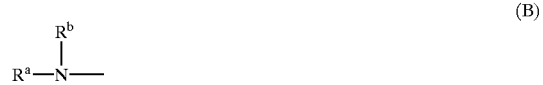

(B)

in which $R^a$ is an alkyl group containing 1 to 20 carbon atoms or is an aryl$C_{1-6}$alkyl group, and $R^b$ is hydrogen or $C_{1-6}$alkyl;

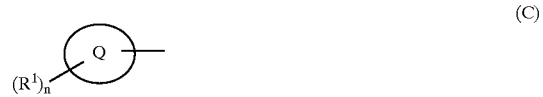

(C)

10 Claims, No Drawings

FOREIGN PATENT DOCUMENTS

| | | | |
|---|---|---|---|
| EP | 0103464 | | 3/1984 |
| EP | 0244115 | | 11/1987 |
| EP | 675118 | * | 10/1994 |
| EP | 675118 | * | 10/1995 |
| EP | 0675118 | | 10/1995 |
| EP | 0815861 | | 1/1998 |
| EP | 815861 | * | 1/1998 |
| WO | 9745419 | * | 12/1997 |

OTHER PUBLICATIONS

Regnier et al,"Chemical and Pharmacologic study of new noradrenaline derivatives",Arzneim.–Forsch., 19/10, 1698–1702(1969).*

Bourson et al,"Determin. of the role of the 5HT6 in rat Brain:",J. Pharm. & Expt. Ther.,274,173(1995).*

Coyle et al,"Alzheimer's Disease:",Science, 2191184(1983).*

* cited by examiner

COMPOUNDS

This invention relates to novel compounds having pharmacological activity, processes for their preparation, to compositions containing them and to their use in the treatment of CNS disorders.

EPA 0 021 580 and EPA 0 076 072 describe naphthyl sulphonamide derivatives which are disclosed as having antiarrhythmic activity. European patent application EP 0815861 discloses a series of aryl sulphonamide compounds that are said to possess $5HT_6$ receptor activity and are useful in the treatment of various CNS disorders. A structurally distinct class of compounds has now been discovered, which also have been found to have $5HT_6$ receptor antagonist activity.

The present invention therefore provides, in a first aspect, a compound of formula (I) or a salt thereof:

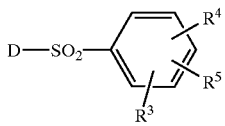
(I)

in which the group D is selected from a group of formula (A), (B) or (C) below:

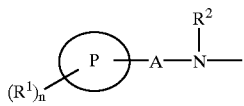
(A)

in which

P is a monocyclic, bicyclic or tricyclic alicyclic ring containing up to 20 carbon atoms in the ring(s);

A is a single bond, a $C_{1-6}$alkylene or a $C_{2-6}$alkenylene group;

$R^1$ is halogen, $C_{1-6}$alkyl optionally substituted by one or more fluorine atoms, $C_{3-6}$cycloalkyl, $C_{1-6}$alkoxy, $OCF_3$, hydroxy, hydroxy$C_{1-6}$alkyl, hydroxy$C_{1-6}$alkoxy, $C_{1-6}$alkoxy$C_{1-6}$alkoxy, $C_{1-6}$alkanoyl, amino, alkylamino or dialkylamino, $SR^{11}$ where $R^{11}$ is hydrogen or $C_{1-6}$alkyl or $R^1$ is aryl, aryl$C_{1-6}$alkyl, a bicyclic heterocyclic ring or is a 5 to 7-membered heterocyclic ring each containing 1 to 4 heteroatoms selected from oxygen, nitrogen or sulphur;

n is 0, 1, 2 or 3; and $R^2$ is hydrogen, $C_{1-6}$alkyl, aryl, aryl$C_{1-6}$alkyl or $C_{3-6}$cycloalkyl; or

(B)

in which $R^a$ is an alkyl group containing 1 to 20 carbon atoms or is an aryl$C_{1-6}$alkyl group, and $R^b$ is hydrogen or $C_{1-6}$alkyl;

(C)

in which Q is a mono-, bi- or tricyclic group containing a nitrogen heteroatom bonded to the adjacent $SO_2$ group or Q is a 5–7 membered heterocyclic ring containing a nitrogen heteroatom bonded to the adjacent $SO_2$ group and a further heteroatom selected from nitrogen, oxygen or sulphur, and $R^1$ and n are as defined above;

$R^3$ is a group $R^5$ or together with $R^5$ forms a group $(CH_2)_2O$ or $(CH_2)_3O$ optionally substituted with 1 or more $C_{1-6}$alkyl groups;

$R^4$ is an optionally substituted piperazine ring; and $R^5$ is hydrogen, halogen, $C_{1-6}$alkyl, $C_{3-6}$cycloalkyl, $C_{1-6}$alkoxy optionally substituted with one or more fluorine atoms, hydroxy, hydroxy$C_{1-6}$alkyl, hydroxy$C_{1-6}$alkoxy, $C_{1-6}$alkoxy$C_{1-6}$alkoxy, $C_{1-6}$alkanoyl, trifluoromethyl, or aryl.

Alkyl groups, whether alone or as part of another group, may be straight chain or branched. The term 'halogen' is used herein to describe, unless otherwise stated, a group selected from fluorine, chlorine, bromine or iodine. The term 'aryl' is used herein to describe, unless otherwise stated, a group such as phenyl or naphthyl. Such aryl groups may be optionally substituted by one or more $C_{1-6}$alkyl or halogen.

Within the Definition of Group D Formula (A)

The group P may be saturated or unsaturated and includes bridged and unbridged bicyclic or tricyclic alicyclic rings, containing saturated and/or unsaturated rings. Examples of the group P which contain both a saturated and an unsaturated ring include indanyl and tetrahydronaphthyl. With such examples the group A is attached to the group P via a carbon atom of the unsaturated ring. When P is a monocyclic ring, suitable examples include cycloalkyl groups containing 4 to 10 carbon atoms e.g. cyclopentyl, cyclohexyl or cycloheptyl. Bicyclic and tricyclic rings may contain, for example, 10 to 20 carbon atoms. Examples of bridged bicyclic groups include bicyclo[2.2.1]heptyl or born-2-yl and examples of bridged tricyclic groups include adamantyl. Preferably P is cyclohexyl.

When $R^1$ is a bicyclic heterocyclic ring, suitable examples include benzothiophene, indole, benzimidazole, quinoline or isoquinoline. Suitable 5 to 7-membered heterocyclic rings include thienyl, furyl, pyrrolyl, triazolyl, imidazolyl, oxazoly, thiazolyl, oxadiazolyl, isothiazolyl, isoxazolyl, thiadiazolyl, pyridyl, pyrimidyl, pyrrolidinyl and pyrazinyl. The heterocyclic rings can be linked to the remainder of the molecule via any suitable carbon atom or, when present, a nitrogen atom. Preferably $R^1$ is a $C_{1-6}$alkyl group such as methyl or ethyl. Preferably n is 0, 1 or 2.

When $R^2$ is a $C_{3-6}$cycloalkyl group a preferred example is cyclohexyl. Preferably $R^2$ is hydrogen or a $C_{1-6}$alkyl group such as methyl, ethyl or isopropyl.

Suitably A is a single bond, a methylene or ethylene group or a —CH=CH—group. Preferably A is a single bond or methylene.

Within the Definition of Group D Formula (B)

The alkyl group $R^a$ may be straight chain or branched. Preferably $R^a$ represents a $C_{1-8}$alkyl group.

Preferably $R^b$ is hydrogen.

Within the Definition of Group D Formula (C)

When Q is a mono-, bi- or tricyclic group containing a single nitrogen heteroatom, suitable examples may be saturated or unsaturated including partially unsaturated groups for example bicyclic groups in which one ring is saturated and the other is unsaturated. Monocyclic groups preferably contain 4 to 8 atoms in the ring, advantageously six atoms, a preferred example of such a monocyclic group being piperidine. Bicyclic groups, which may be bridged or unbridged, preferably contain 8 to 12 atoms in the rings, advantageously 10 atoms, preferred examples of such bicyclic groups being decahydroquinoline or decahydroisoquinoline. Tricyclic groups, which may be bridged or unbridged, preferably contain 6 to 14 atoms in the rings. When Q is a 5–7 membered heterocyclic ring containing a further heteroatom, suitable examples include piperazinyl, morpholinyl or thiomorpholinyl.

When $R^1$ is a bicyclic heterocyclic ring or a 5–7 membered heterocylic ring suitable examples include those listed for $R^1$ within the definition of formula (A). Preferably $R^1$ is a $C_{1-6}$alkyl group such as methyl or ethyl or an aryl$C_{1-6}$alkyl group such as benzyl. Preferably n is 0, 1 or 2.

$R^3$ is a group $R^5$ or together with $R^5$ forms a group $(CH_2)_2O$ or $(CH_2)_3O$. It will be appreciated that when $R^3/R^5$ groups are linked together the two groups must be attached to adjacent carbon atoms of the phenyl ring. Preferably $R^3$ is a group $R^5$, in particular hydrogen.

Preferably $R^4$ is meta with respect to the $SO_2$ group. Optional substituents for the piperazine ring, which can be present on carbon and/or nitrogen atoms, include $C_{1-6}$alkyl, in particular methyl. Most preferably $R^4$ is unsubstituted piperazine.

Suitably $R^5$ is $C_{1-6}$alkoxy. Preferably $R^5$ is a methoxy group with a para relationship with respect to the $SO_2$ group.

Particular compounds of the invention include:
N-Cyclohexyl-4-methoxy-3-piperazin-1-ylbenzenesulfonamide,
N-Indan-1-yl-4-methoxy-3-piperazin-1-ylbenzenesulfonamide,
N-Bicyclo[2.2.1]hept-2-yl-4-methoxy-3-piperazin-1-ylbenzenesulfonamide,
N-Adamantan-1-yl-4-methoxy-3-piperazin-1-ylbenzenesulfonamide,
N-Cycloheptyl-4-methoxy-3-piperazin-1-ylbenzenesulfonamide,
N-Cyclohexyl-4-methoxy-N-methyl-3-piperazin-1-ylbenzenesulfonamide,
N-Adamantan-2-yl-4-methoxy-3-piperazin-1-ylbenzenesulfonamide,
N-Cyclopentyl-4-methoxy-3-piperazin-1-ylbenzenesulfonamide,
1-[5-(4-Benzylpiperidine-1-sulfonyl)]-2-methoxyphenyl]piperazine,
N-Hexyl-4-methoxy-3-piperazin-1-ylbenzenesulfonamide,
N-Indan-2-yl-4-methoxy-3-piperazin-1-ylbenzenesulfonamide,
1-[5-(3,3-Dimethylpiperidine-1-sulfonyl)]-2-methoxyphenyl]piperazine,
1-[5-(2-Ethylpiperidine-1-sulfonyl)]-2-methoxyphenyl]piperazine,
4-Methoxy-N-(1-methylbutyl)-3-piperazin-1-ylbenzenesulfonamide,
N-tert-Butyl-4-methoxy-3-piperazin-1-ylbenzenesulfonamide,
(R)-4-Methoxy-3-piperazin-1-yl-N-(1,7,7-trimethylbicyclo[2.2.1]hept-2-yl)-benzenesulfonamide,
N-(4-tert-Butylcyclohexyl)-4-methoxy-3-piperazin-1-ylbenzenesulfonamide,
4-Methoxy-N-(2-methylcyclohexyl)-3-piperazin-1-ylbenzenesulfonamide,
4-Methoxy-N-(3-methylcyclohexyl)-3-piperazin-1-ylbenzenesulfonamide,
4-Methoxy-N-(4-methylcyclohexyl)-3-piperazin-1-ylbenzenesulfonamide,
N-(2,3-Dimethylcyclohexyl)-4-methoxy-3-piperazin-1-ylbenzenesulfonamide,
1-(4-Methoxy-3-piperazin-1-ylbenzenesulfonyl)decahydroquinoline,
2-(4-Methoxy-3-piperazin-1-ylbenzenesulfonyl)decahydroisoquinoline,
N-[2-(4-Fluoro-phenyl)-1,1-dimethyl-ethyl]-4-methoxy-3-piperazin-1-yl-benzenesulfonamide,
N-(1,1-Dimethyl-propyl)-4-methoxy-3-piperazin-1-yl-benzenesulfonamide,
N-Cyclohexyl-4-methoxy-N-phenyl-3-piperazin-1-yl-benzenesulfonamide,
N,N-Dicyclohexyl-4-methoxy-3-piperazin-1-yl-benzenesulfonamide,
N-(1-(R)-Cyclohexyl-ethyl)-4-methoxy-3-piperazin-1-yl-benzenesulfonamide,
N-(1-(S)-Cyclohexyl-ethyl)-4-methoxy-3-piperazin-1-yl-benzenesulfonamide,
N-Cyclohexyl-N-ethyl-4-methoxy-3-piperazin-1-yl-benzenesulfonamide,
N-Cyclohexyl-N-isopropyl-4-methoxy-3-piperazin-1-yl-benzenesulfonamide,
4-(4-Methoxy-3-piperazin-1-ylbenzenesulfonyl)morpholine,
4-(4-Methoxy-3-piperazin-1-ylbenzenesulfonyl)thiomorpholine,
4-Methoxy-3-piperazin-1-yl-N-(1,1,3,3-tetramethylbutyl)benzenesulfonamide an pharmaceutically acceptable salts thereof.

The compounds of the formula (I) can form acid addition salts with acids, such as conventional pharmaceutically acceptable acids, for example maleic, hydrochloric, hydrobromic, phosphoric, acetic, fumaric, salicylic, citric, lactic, mandelic, tartaric and methanesulphonic.

Compounds of formula (I) may also form solvates such as hydrates, and the invention also extends to these forms. When referred to herein, it is understood that the term 'compound of formula (I)' also includes these forms.

Certain compounds of formula (I) are capable of existing in stereoisomeric forms including diastereomers and enantiomers and the invention extends to each of these stereoisomeric forms and to mixtures thereof including racemates. The different stereoisomeric forms may be separated one from the other by the usual methods, or any given isomer may be obtained by stereospecific or asymmetric synthesis. The invention also extends to any tautomeric forms and mixtures thereof.

The present invention also provides a process for the preparation of a compound of formula (I) or a pharmaceutically acceptable salt thereof, which process comprises the coupling of a compound of formula (II):

$$D-H \qquad (II)$$

in which D is as defined in formula (I) or protected derivatives thereof with a compound of formula (III):

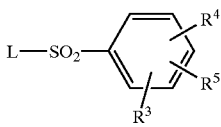

(III)

in which $R^3$, $R^4$ and $R^5$ are as defined in formula (I) or protected derivatives thereof and L is a leaving group and optionally thereafter:

removing any protecting groups, forming a pharmaceutically acceptable salt.

Suitable leaving groups include halogen, in particular chloro. The reaction of a compounds of formulae (II) and (III) is carried out by mixing the two reagents together, optionally in an inert solvent such as dichloromethane with or without the addition of a suitable base such as triethylamine.

Those skilled in the art will appreciate that it may be necessary to protect certain groups. Suitable protecting groups and methods for their attachment and removal are conventional in the art of organic chemistry, such as those described in Greene T. W. 'Protective groups in organic synthesis' New York, Wiley (1981).

Compounds of formulae (II) and (III) are commercially available or may be prepared according to known methods or analogous to known methods.

Pharmaceutically acceptable salts may be prepared conventionally by reaction with the appropriate acid or acid derivative.

Compounds of formula (I) and their pharmaceutically acceptable salts have $5HT_6$ receptor antagonist activity and are believed to be of potential use in the treatment of certain CNS disorders such as anxiety, depression, epilepsy, obsessive compulsive disorders, migraine, cognitive memory disorders e.g. Alzheimers disease, Parkinson' Disease, ADHD (Attention Deficit Disorder/Hyperactivity Syndrome), sleep disorders (including disturbances of Circadian rhythym), feeding disorders such as anorexia and bulimia, panic attacks, withdrawal from drug abuse such as cocaine, ethanol, nicotine and benzodiazepines, schizophrenia, and also disorders associated with spinal trauma and/or head injury such as hydrocephalus. Compounds of the invention are also expected to be of use in the treatment of certain GI (gastrointestinal) disorders such as IBS (Irritable Bowel Syndrome).

Thus the invention also provides a compound of formula (I) or a pharmaceutically acceptable salt thereof, for use as a therapeutic substance, in particular in the treatment or prophylaxis of the above disorders.

The invention further provides a method of treatment or prophylaxis of the above disorders, in mammals including humans, which comprises administering to the sufferer a therapeutically effective amount of a compound of formula (I) or a pharmaceutically acceptable salt thereof.

In another aspect, the invention provides the use of a compound of formula (I) or a pharmaceutically acceptable salt thereof in the manufacture of a medicament for the treatment or prophylaxis of the above disorders.

The present invention also provides a pharmaceutical composition, which comprises a compound of formula (I) or a pharmaceutically acceptable salt thereof, and a pharmaceutically acceptable carrier.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusable solutions or suspensions or suppositories. Orally administrable compositions are generally preferred.

Tablets and capsules for oral administration may be in unit dose form, and may contain conventional excipients, such as binding agents, fillers, tabletting lubricants, disintegrants and acceptable wetting agents. The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparazins may contain conventional additives such as suspending agents, emulsifying agents, non-aqueous vehicles (which may include edible oils), preservatives, and, if desired, conventional flavourings or colourants.

For parenteral administration, fluid unit dosage forms are prepared utilising a compound of the invention or pharmaceutically acceptable salt thereof and a sterile vehicle. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilised by exposure to ethylene oxide before suspension in a sterile vehicle. Advantageously, a surfactant or wetting agent is included in the composition to facilitate uniform distribution of the compound.

The composition may contain from 0.1% to 99% by weight, preferably from 10 to 60% by weight, of the active material, depending on the method of administration.

The dose of the compound used in the treatment of the aforementioned disorders will vary in the usual way with the seriousness of the disorders, the weight of the sufferer, and other similar factors. However, as a general guide suitable unit doses may be 0.05 to 1000 mg, more suitably 0.05 to 20.0 mg, for example 0.2 to 5 mg; and such unit doses may be administered more than once a day, for example two or three a day, so that the total daily dosage is in the range of about 0.5 to 100 mg; and such therapy may extend for a number of weeks or months.

When administered in accordance with the invention, no unacceptable toxicological effects are expected with the compounds of the invention.

The following Descriptions and Examples illustrate the preparation of compounds of the invention.

Description 1

2-(4-Trichloroacetylpiperazin-1-yl) anisole (D1)

A solution of 1-(2-methoxyphenyl) piperazine (7.0 g) in dichloromethane (30 ml) was added over 15 minutes to a stirred solution of trichloroacetyl chloride (4.06 ml) in dichloromethane (40 ml) at room temperature under argon. Diisopropylethylamine (5.95 ml) was then added and the whole was stirred for 18 hours. The reaction mixture was washed with water (2×100 ml), dried (Na$_2$SO4) and concentrated to give the title compound (D1) as an oil (11.2 g, 91%), MH+337/339.

Description 2

3-(4-Trichloroacetylpiperazin-1-yl)-4-methoxybenzenesulfonyl chloride (D2)

A solution of 2-(4-trichloroacetylpiperazin-1-yl) anisole (D1) (10 g) in dichloromethane (115 ml) was added over 0.3 h to ice-cooled chlorosulfonic acid (52 ml). After 0.5 h at 0° C. then 1 hour at ambient temperature, the solution was poured onto a mixture of ice-water (500 g) and dichloromethane (500 ml) with rapid stirring. The layers were separated and the organic phase was washed with water (2×800 ml), dried ($MgSO_4$) and concentrated to give the title compound (D2) as a foam (6.0 g, 46%), MH+ 435/437.

EXAMPLE 1

N-Cyclohexyl-4-methoxy-3-piperazin-1-ylbenzenesulfonamide hydrochloride (E1)

A solution of cyclohexylamine (91 mg) in dichloromethane (1 ml) was added slowly to a stirred solution of 3-(4-trichloroacetylpiperazin-1-yl)-4-methoxybenzenesulfonyl chloride (D2) (200 mg) in dichloromethane (2 ml). The mixture was stirred overnight then washed with 1M HCl (4 ml) and water (4 ml), dried and concentrated to a solid. The solid was dissolved in tetrahydrofuran or 1,4-dioxane (5 ml) and to the solution was added 0.15M potassium hydroxide solution (5 ml) and the whole stirred at ambient temperature for 8 hours. The solution was concentrated to remove the organic solvent and the aqueous residue was extracted with dichloromethane (2×20 ml). The combined extracts were dried, acidified with 1M ethereal hydrogen chloride (1 ml), concentrated to an oil and stirred with acetone/diethyl ether to afford the title compound (E1) (28 mg, 21%). δH (250 MHz, d6-DMSO) 1.10 (5H, br, s), 1.56 (5H, br, s), 2.86 (1H, br, s), 3.21 (8H, br, s), 3.87 (3H, s), 7.13 (1H, d, J=8.0 Hz), 7.33 (1H, s), 7.46–7.52 (2H, m), 9.19 (2H, br, s), MH+354.

EXAMPLE 2

N-Indan-1-yl-4-methoxy-3-piperazin-1-ylbenzenesulfonamide hydrochloride (E2)

To a stirred solution of 3-(4-Trichloroacetylpiperazin-1-yl)-4-methoxybenzenesulfonyl chloride (0.46 mmol) in dichloromethane (2 ml) was added a solution of amine (1 mmol) in dichloromethane (1 ml). The mixture was stirred at ambient temperature overnight, then dichloromethane (4 ml) was added and the resulting solution was washed with 1M HCl (4 ml) and water (4 ml), dried ($Na_2SO_4$) and concentrated to a solid. The solid was dissolved in 1,4-dioxane (9 ml) or 1,4-dioxane:tetrahydrofurane (5:4, v/v, 9 ml), 1M aqueous potassium hydroxide (1 ml) was added and the reaction was stirred at ambient temperature for 17 hours. The solvent was partially removed, water was added (5 ml) and the solution was extracted with dichloromethane (2×10 ml). The combined extracts were dried ($Na_2SO_4$) and evaporated to dryness. The residue was redissolved in dichloromethane (2 ml), acidified with 1M hydrogen chloride in diethyl ether (1 ml) and concentrated to afford the title compound as a solid (E2) (177 mg, 91%), MH+ 388.

The following compounds were prepared by a similar method to that described in Example 2 using the appropriate amine. All amines are either commercially available or can be prepared according to literature procedures.

| Compound | MH+ |
| --- | --- |
| N-Bicyclo[2.2.1]hept-2-yl-4-methoxy-3-piperazin-1-ylbenzenesulfonamide (E3) | 366 |
| N-Adamantan-1-yl-4-methoxy-3-piperazin-1-ylbenzenesulfonamide (E4) | 406 |
| N-Cycloheptyl-4-methoxy-3-piperazin-1-ylbenzenesulfonamide (E5) | 368 |
| N-Cyclohexyl-4-methoxy-N-methyl-3-piperazin-1-ylbenzenesulfonamide(E6) | 368 |
| N-Adamantan-2-yl-4-methoxy-3-piperazin-1-ylbenzenesulfonamide (E7) | 406 |
| N-Cyclopentyl-4-methoxy-3-piperazin-1-ylbenzenesulfonamide (E8) | 340 |
| 1-[5-(4-Benzylpiperidine-1-sulfonyl)]-2-methoxyphenyl]piperazine (E9) | 430 |
| N-Hexyl-4-methoxy-3-piperazin-1-ylbenzenesulfonamide (E10) | 356 |
| N-Indan-2-yl-4-methoxy-3-piperazin-1-ylbenzensulfonamide (E11) | 388 |
| 1-[5-(3,3-Dimethylpiperidine-1-sulfonyl)]-2-methoxyphenyl]piperazine (E12) | 368 |
| 1-[5-(2-Ethylpiperidine-1-sulfonyl)]-2-methoxyphenyl]piperazine (E13) | 368 |
| 4-Methoxy-N-(1-methylbutyl)-3-piperazin-1-ylbenzenesulfonamide (E14) | 342 |
| N-tert-Butyl-4-methoxy-3-piperazin-1-ylbenzenesulfonamide (E15) | 328 |
| (R)-4-Methoxy-3-piperazin-1-yl-N-(1,7,7-trimethylbicyclo[2.2.1]hept-2-yl)-benzenesulfonamide (E16) | 408 |
| N-(4-tert-Butylcyclohexyl)-4-methoxy-3-piperazin-1-ylbenzenesulfonamide (E17) | 410 |
| 4-Methoxy-N-(2-methylcyclohexyl)-3-piperazin-1-ylbenzenesulfonamide (E18) | 368 |
| 4-Methoxy-N-(3-methylcyclohexyl)-3-piperazin-1-ylbenzenesulfonamide (E19) | 368 |
| 4-Methoxy-N-(4-methylcyclohexyl)-3-piperazin-1-ylbenzenesulfonamide (E20) | 368 |
| N-(2,3-Dimethylcyclohexyl)-4-methoxy-3-piperazin-1-ylbenzenesulfonamide (E21) | 382 |
| 1-(4-Methoxy-3-piperazin-1-ylbenzenesulfonyl)decahydroquinoline (E22) | 394 |
| 2-(4-Methoxy-3-piperazin-1-ylbenzenesulfonyl)decahydroisoquinoline (E23) | 394 |
| N-[2-(4-Fluoro-phenyl)-1,1-dimethyl-ethyl]-4-methoxy-3-piperazin-1-yl-benzenesulfonamide (E24) | 422 |
| N-(1,1-Dimethyl-propyl)4-methoxy-3-piperazin-1-yl-benzenesulfonamide (E25) | 342 |
| N-Cyclohexyl-4-methoxy-N-phenyl-3-piperazin-1-yl-benzenesulfonamide (E26) | 430 |
| N,N-Dicyclohexyl-4-methoxy-3-piperazin-1-yl-benzenesulfonamide (E27) | 436 |
| N-(1-(R)-Cyclohexyl-ethyl)-4-methoxy-3-piperazin-1-yl-benzenesulfonamide (E28) | 382 |
| N-(1-(S)-Cyclohexyl-ethyl)-4-methoxy-3-piperazin-1-yl-benzenesulfonamide (E29) | 382 |
| N-Cyclohexyl-N-ethyl-4-methoxy-3-piperazin-1-yl-benzenesulfonamide (E30) | 382 |
| N-Cyclohexyl-N-isopropyl-4-methoxy-3-piperazin-1-yl-benzenesulfonamide (E31) | 396 |
| 4-(4-Methoxy-3-piperazin-1-ylbenzenesulfonyl)morpholine (E32) | 342 |
| 4-(4-Methoxy-3-piperazin-1-ylbenzensulfonyl)thiomorpholine (E33) | 358 |
| 4-Methoxy-3-piperazin-1-yl-N-(1,1,3,3-tetramethylbutyl)benzenesulfonamide (E34) | 384 |

Pharmacological Data

Compounds can be tested following the procedures outlined in WO 98/27081. All compounds tested showed good affinity for the 5-$HT_6$ receptor, having pKi values 7.4–8.8 at human cloned 5-$HT_6$ receptors. Particularly preferred compounds demonstrated pKi>7.9 and >100 fold selectivity. Examples of such compounds include:

E1, E3–7, E17–22, E27, E30–31.

What is claimed is:

1. A compound of formula (I) or a salt thereof:

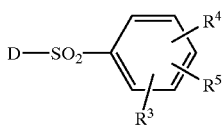
(I)

in which the group D is selected from a group of formula (A), (B) or (C) below:

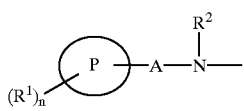
(A)

in which
P is a monocyclic alicyclic ring containing 4–10 carbon atoms;
A is a single bond, a $C_{1-6}$alkylene or a $C_{2-6}$alkenylene group;
$R^1$ is halogen, $C_{1-6}$alkyl optionally substituted by one or more fluorine atoms, $C_{3-6}$cycloalkyl, $C_{1-6}$alkoxy, $OCF_3$, hydroxy, hydroxy$C_{1-6}$alkyl, hydroxy$C_{1-6}$alkoxy, $C_{1-6}$alkoxy$C_{1-6}$alkoxy, $C_{1-6}$alkanoyl, amino, alkylamino or dialkylamino, $SR^{11}$ where $R^{11}$ is hydrogen or $C_{1-6}$alkyl or $R^1$ is aryl, or aryl$C_{1-6}$alkyl;
n is 0, 1, 2 or 3; and
$R^2$ is hydrogen, $C_{1-6}$alkyl, aryl, aryl$C_{1-6}$alkyl or $C_{3-6}$cycloalkyl; or

(B)

in which $R^a$ is an alkyl group containing 1 to 20 carbon atoms or is an aryl$C_{1-6}$alkyl group, and $R^b$ is hydrogen; or

(C)

in which Q is a monocyclic group containing a nitrogen heteroatom bonded to the adjacent $SO_2$ group or Q is a 5 or 6-membered heterocyclic ring containing a nitrogen heteroatom bonded to the adjacent $SO_2$ group and a further heteroatom selected from nitrogen, oxygen or sulphur, and $R^1$ and n are as defined above;
$R^3$ is a group $R^5$;
$R^4$ is a piperazine ring optionally substituted by $C_{1-6}$alkyl;
$R^5$ is hydrogen, halogen, $C_{1-6}$alkyl, $C_{3-6}$cycloalkyl, $C_{1-6}$alkoxy optionally substituted with one or more fluorine atoms, hydroxy, hydroxy$C_{1-6}$alkyl, hydroxy$C_{1-6}$ alkoxy, $C_{1-6}$alkoxy$C_{1-6}$alkoxy, $C_{1-6}$alkanoyl or trifluoromethyl.

2. A compound according to claim 1 in which P is cyclohexyl.

3. A compound according to claim 1 in which Q is piperdine.

4. A compound according to claim 3 in which $R^1$ is $C_{1-6}$alkyl.

5. A compound according to claim 4 in which $R^4$ is an unsubstituted piperazine ring.

6. A compound according to claim 5 in which $R^5$ is methoxy.

7. A compound according to claim 1 which is selected from the group consisting of:
N-Cyclohexyl-4-methoxy-3-piperazin-1-ylbenzenesulfonamide,
N-Cycloheptyl-4-methoxy-3-piperazin-1-ylbenzenesulfonamide,
N-Cyclohexyl-4-methoxy-N-methyl-3-piperazin-1-ylbenzenesulfonamide,
N-Cyclopentyl-4-methoxy-3-piperazin-1-ylbenzenesulfonamide,
1-[5-(4-Benzylpiperidine-1-sulfonyl)]-2-methoxyphenyl]piperazine,
N-Hexyl-4-methoxy-3-piperazin-1-ylbenzenesulfonamide,
1-[5-(3,3-Dimethylpiperidine-1-sulfonyl)]-2-methoxyphenyl]piperazine,
1-[5-(2-Ethylpiperidine-1-sulfonyl)]-2-methoxyphenyl]piperazine,
4-Methoxy-N-(1-methylbutyl)-3-piperazin-1-ylbenzenesulfonamide,
N-tert-Butyl-4-methoxy-3-piperazin-1-ylbenzenesulfonamide,
N-(4-tert-Butylcyclohexyl)-4-methoxy-3-piperazin-1-ylbenzenesulfonamide,
4-Methoxy-N-(2-methylcyclohexyl)-3-piperazin-1-ylbenzenesulfonamide,
4-Methoxy-N-(3-methylcyclohexyl)-3-piperazin-1-ylbenzenesulfonamide,
4-Methoxy-N-(4-methylcyclohexyl)-3-piperazin-1-ylbenzenesulfonamide,
N-(2,3-Dimethylcyclohexyl)-4-methoxy-3-piperazin-1-ylbenzenesulfonamide,
N-[2-(4-Fluoro-phenyl)-1,1-dimethyl-ethyl]-4-methoxy-3-piperazin-1-yl-benzenesulfonamide,
N-(1,1-Dimethyl-propyl)4-methoxy-3-piperazin-1-yl-benzenesulfonamide,
N-Cyclohexyl-4-methoxy-N-phenyl-3-piperazin-1-yl-benzenesulfonamide,
N,N-Dicyclohexyl-4-methoxy-3-piperazin-1-yl-benzenesulfonamide,
N-(1-(R)-Cyclohexyl-ethyl)-4-methoxy-3-piperazin-1-yl-benzenesulfonamide,
N-(1-(S)-Cyclohexyl-ethyl)-4-methoxy-3-piperazin-1-yl-benzenesulfonamide,
N-Cyclohexyl-N-ethyl-4-methoxy-3-piperazin-1-yl-benzenesulfonamide,
N-Cyclohexyl-N-isopropyl-4-methoxy-3-piperazin-1-yl-benzenesulfonamide,
4-(4-Methoxy-3-piperazin-1-ylbenzenesulfonyl)morpholine,
4-(4-Methoxy-3-piperazin-1-ylbenzenesulfonyl)thiomorpholine, and
4-Methoxy-3-piperazin-1-yl-N-(1,1,3,3,-tetramethylbutyl)benzenesulfonamide
and pharmaceutically acceptable salts thereof.

8. A process for the preparation of a compound of formula (I) or a pharmaceutically acceptable salt thereof, which process comprises the coupling of a compound of formula (II):

D—H          (II)

in which D is as defined in formula (I) or protected derivatives thereof with a compound of formula (III):

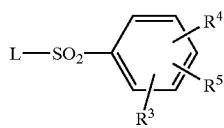 (III)

in which R³, R⁴ and R⁵ are as defined in formula (I) or protected derivatives thereof and L is a leaving group by mixing the two reagents together with or without an inert solvent with or without the addition of a suitable base, and optionally thereafter removing any protecting groups;

forming a pharmaceutically acceptable salt.

9. A pharmaceutical composition which comprises a compound according to claim 1 and a pharmaceutically acceptable carrier or excipient.

10. A method of treating Alzheimer's disease, schizophrenia or depression comprising administering to a patient in need of treatment a safe and therapeutically effective amount of a compound according to claim 1.

\* \* \* \* \*